(12) United States Patent
Cheng

(10) Patent No.: US 6,514,284 B1
(45) Date of Patent: Feb. 4, 2003

(54) STENT HAVING INNER FLOW CHANNELS

(75) Inventor: E Tina Cheng, Piedmont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/553,589

(22) Filed: Apr. 20, 2000

(51) Int. Cl.[7] .................................................. A61F 2/06
(52) U.S. Cl. ..................................... 623/1.15; 623/1.44
(58) Field of Search .............................. 623/1.15, 1.13, 623/1.16, 1.27, 1.44, 1.45; 606/198, 191, 195

(56) References Cited

U.S. PATENT DOCUMENTS

| | | | |
|---|---|---|---|
| 4,130,904 A | * | 12/1978 | Whalen ...................... 623/1.13 |
| 5,108,417 A | | 4/1992 | Sawyer |
| RE34,327 E | | 7/1993 | Kreamer |
| 5,344,425 A | * | 9/1994 | Sawyer ........................ 606/198 |
| 5,486,191 A | | 1/1996 | Pasricha et al. |
| 5,645,559 A | | 7/1997 | Hachtman et al. |
| 5,709,702 A | | 1/1998 | Cogita |
| 5,718,713 A | | 2/1998 | Frantzen |
| 5,728,150 A | | 3/1998 | McDonald et al. |
| 5,746,691 A | | 5/1998 | Frantzen |
| 5,749,880 A | | 5/1998 | Banas et al. |
| 5,776,160 A | | 7/1998 | Pasricha et al. |
| 5,782,905 A | | 7/1998 | Richter |
| 5,785,679 A | | 7/1998 | Abolfathi et al. |
| 5,792,106 A | | 8/1998 | Mische |
| 5,795,318 A | | 8/1998 | Wang et al. |
| 5,824,046 A | | 10/1998 | Smith et al. |
| 5,843,163 A | | 12/1998 | Wall |
| 5,925,061 A | | 7/1999 | Ogi et al. |
| 5,957,975 A | | 9/1999 | Lafont et al. |
| 6,004,328 A | | 12/1999 | Solar |
| 6,033,435 A | | 3/2000 | Penn et al. |
| 6,036,725 A | | 3/2000 | Avellanet |
| 6,039,757 A | | 3/2000 | Edwards et al. |
| 6,096,070 A | * | 8/2000 | Ragheb et al. .............. 623/1.44 |

* cited by examiner

*Primary Examiner*—Kevin T. Truong
(74) *Attorney, Agent, or Firm*—Fulwider Patton Lee & Utecht, LLP

(57) ABSTRACT

A stent having an expandable inner layer and a channel thereon to direct blood flow and induce a rotational motion therein, thereby increasing the speed of blood flowing through the stent and reducing the likelihood of blood clotting, thrombosis, and restenosis.

8 Claims, 2 Drawing Sheets

STENT HAVING INNER FLOW CHANNELS

BACKGROUND OF THE INVENTION

The present invention relates generally to expandable endoprosthesis devices, generally called stents, which are adapted to be implanted into a patient's body lumen, such as a blood vessel, to maintain the patency thereof, and more particularly to vascular stents that are formed with flow channels to accelerate blood flow therethrough and minimize clot and thrombus formation.

Stents are particularly useful in the treatment and repair of blood vessels after a stenosis has been compressed by percutaneous transluminal coronary angioplasty (PTCA), percutaneous transluminal angioplasty (PTA), or removed by atherectomy or other means, to help improve the results of the procedure and reduce the possibility of restenosis. Stents also can be used to provide primary compression to a stenosis in cases in which no initial PTCA or PTA procedure is performed. While stents are most often used in the procedures mentioned above, they also can be implanted in another body lumen such as the urethra, esophagus and bile duct.

In typical PTCA procedures, a guiding catheter or sheath is percutaneously introduced into the cardiovascular system of a patient through the femoral arteries and advanced through the vasculature until the distal end of the guiding catheter is in the aorta. A guidewire and a dilatation catheter having a balloon on the distal end are introduced through the guiding catheter with the guidewire sliding within the dilatation catheter. The guidewire is first advanced out of the guiding catheter into the patient's vasculature and is advanced across the arterial lesion. The dilatation catheter is subsequently advanced over the previously advanced guidewire until the dilatation balloon is properly positioned across the arterial lesion. Once in position across the lesion, the expandable balloon is inflated to a predetermined size with a radiopaque liquid at relatively high pressure to displace the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of abrupt reclosure and to strengthen the area, a physician can implant an intravascular prosthesis for maintaining vascular patency, commonly known as a stent, inside the artery across the lesion. Stents are generally cylindrically shaped devices which function to hold open and sometimes expand a segment of a blood vessel or other arterial lumen, such as coronary artery. Stents are usually delivered in a compressed condition to the target location and then are deployed into an expanded condition to support the vessel and help maintain it in an open position. The stent is usually crimped tightly onto a delivery catheter and transported in its delivery diameter through the patient's vasculature. The stent is expandable upon application of a controlled force, often through the inflation of the balloon portion of the delivery catheter, which expands the compressed stent to a larger diameter to be left in place within the artery at the target location. The stent also may be of the self-expanding type formed from, for example, shape memory metals or super-elastic nickel-titanium (NiTi) alloys, which will automatically expand from a compressed state when the stent is advanced out of the distal end of the delivery catheter into the body lumen.

At present, there are numerous commercial stents being marketed throughout the world. The use of stents has so far been plagued by certain common problems, including the formation of thrombi and blood clots, and the occurrence of restenosis. Thrombosis is a phenomenon whereby a fibrous clot forms within small cracks and other irregularities in an object, such as may be found on the surface of a stent. Furthermore, turbulence in the blood flow caused by abrupt edges on the stent can also produce stagnant pools of blood, thereby encouraging the deposition of plaque and other materials and the formation of blood clots. In addition, blood flow turbulence is suspected to play in role in the causation of restenosis, wherein the vessel walls thicken in response to the trauma induced by the expanding stent.

Hence, in light of the above, those skilled in the art have recognized a need for a stent to implant in a body vessel that will reduce the likelihood of thrombosis, restenosis, and blood clotting. The present invention satisfies these needs as well as others.

SUMMARY OF THE INVENTION

The present invention addresses the above mentioned needs by providing a stent that induces a rotational motion in blood flowing therethrough, thus lessening the likelihood of thrombus and blood clot formation.

Briefly and in general terms, in one aspect the present invention is directed to a stent with an inner layer that is formed with a channel along its inner surface. The channel extends generally between the ends of the stent and directs a portion of the blood flowing therethrough in a generally circular direction with respect to the normal direction of blood flow.

In another aspect, the layer is formed with multiple channels to direct blood flow. The channel or channels may extend around the longitudinal axis of the stent forming a plurality of turns, thus describing a helix, to less than a full, 360 degree turn to impart only a slight rotational motion to the blood flow.

More specifically, the layer includes a polymeric material that has a channel cut by a laser or a blade or equivalent thereof while the polymeric material is in the form of a sheet, following which the sheet is rolled up to form a structure suitable to attaching to the interior of a stent. Alternatively, the channel may be formed by a strip disposed on the polymeric sheet to define the channel. In a still further embodiment, the inner layer may be cast as a unitary, generally tubular piece with the channel impressed into the layer by the casting mold.

DETAILED DESCRIPTION OF THE PREFERRED EMBODIMENTS

Figure 1:
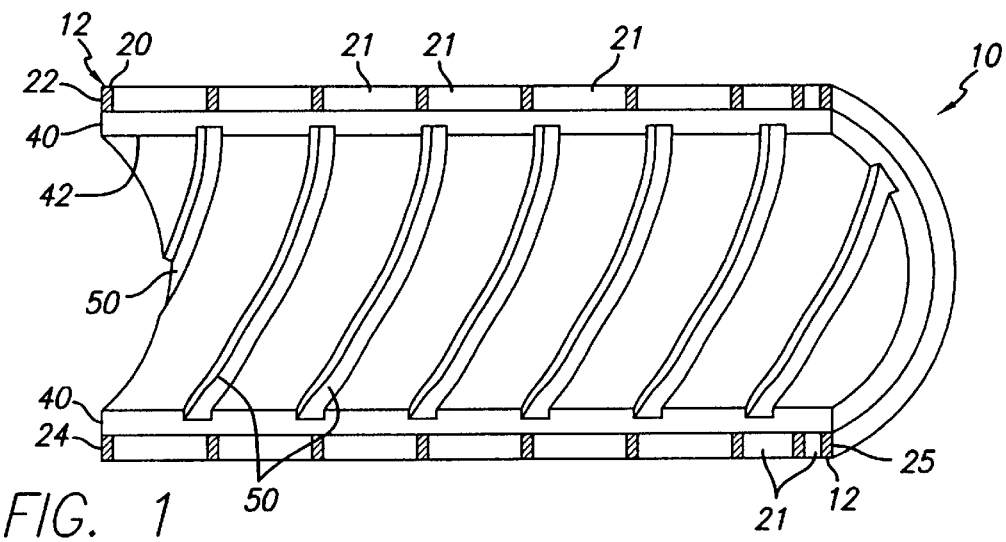
FIG. 1 is a cross-sectional side view of a stent depicting an inner flow channel according to the invention.

Turning now to the drawings, in which like reference numerals are used to designate like or corresponding elements among the several figures, in FIG. 1 there is shown a stent 10 formed according to the invention of an expandable, generally tubular body 12 and an inner layer 40 disposed on an inner surface 22 of the tubular body. The body is defined by a cylindrical wall 20 extending between a first end 24 and a second end 25. The particular structure of the tubular body can take any form, and it is generally irrelevant to the practice of the invention described herein. Stents are typically in the shape of a tubular body with various apertures 21 formed in the cylindrical wall of body to enable the radial expansion of the tube by an inner force, such as that expended by an inflation balloon. Preferably, the stent includes metallic stents, structures formed of laser cut tubes defining a pattern having apertures, and polymeric and metallic tubes with expandable patterns of apertures formed therein by laser cutting or chemical etching or any other process.

With continued reference to FIG. 1, an inner layer 40 is disposed along the inner surface 22 to extend substantially the entire length of the tubular body 12 and cover the apertures 21 to prevent blood flowing through the stent 10 from entering the apertures. The layer thus prevents the apertures from providing zones of turbulent blood flow as well as pockets in which blood clots or thrombi may form, and thus enhances the biocompatibility and safety of the stent of the present invention. The inner layer 40 must thus closely adhere to inner surface 22 of the cylindrical body 12, and preferably embodiment is attached to the inner surface with a bonding agent or adhesive which can be silicone adhesive or dimethyl acetaminide (DMAC), or a known thermal adhesive. A silicone primer can be placed initially on the inner surface to facilitate the chemical bond between the inner surface and the inner layer.

The inner layer 40 is attached to the tubular body 12 prior to implantation, and thus the inner layer must be able to expand along with the body when the stent 10 is expanded within a body lumen. Thus, in one embodiment, the inner layer is formed of a polymeric material such as silastic rubber or Teflon©. Other materials may be used to form the inner layer provided that they are biocompatible, non-toxic, impermeable to blood, and have the requisite expandability. The material of the inner layer would preferably deform plastically upon expansion, thereby minimizing the stress placed upon the bond between the inner layer and the inner surface of the tubular body.

Figure 2:
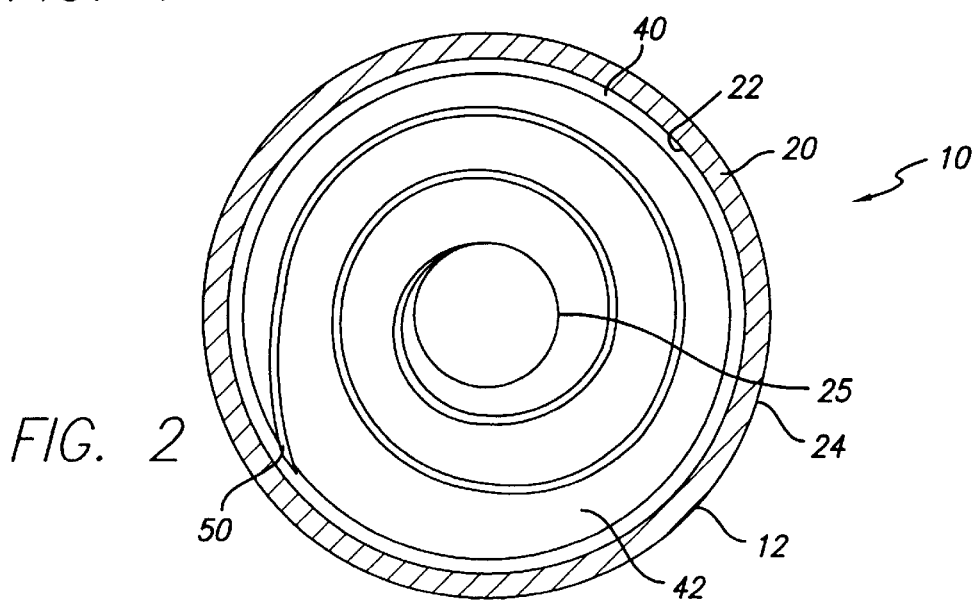
FIG. 2 is a front view depicting the stent of FIG. 1.
Figure 3:
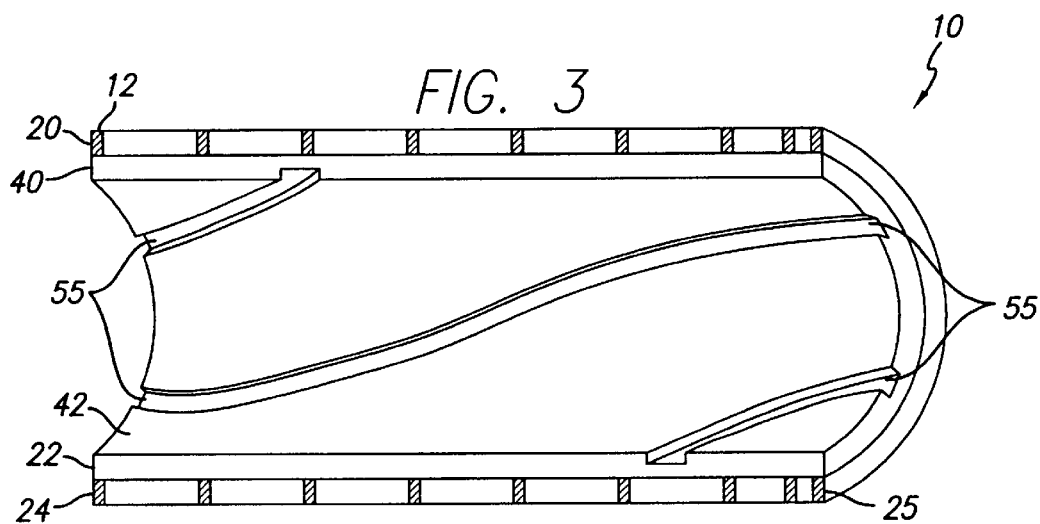
FIG. 3 is a cross-sectional side view depicting an alternative embodiment of the stent of the invention.

With reference to FIGS. 1 and 2, the inner layer 40 is further formed with a channel 50 along its inner surface 42. In the preferred embodiment shown in FIGS. 1 and 2, the channel extends multiple times around the circumference of the inner layer to describe a helical path that extends from the first end 24 to the second end 25. Alternatively, as shown in FIG. 3, the inner layer 40 may be formed with multiple channels 55 that curve around the circumference of the inner layer as they extend from the first end to second end. The channels 50 and 55 are shown with a rectangular cross section, but those skilled in the art will understand that all other channel configurations are also envisioned (e.g., "C-shaped") for use with the present invention. The purpose of forming channels on the inner surface of the inner layer is to provide a flow path for the blood flowing through the stent that is directed partially along the circumference of the inner layer, and thus at an angle to the longitudinal axis of the stent and the normal direction of blood flow.

The purpose of inducing rotational motion in the blood molecules flowing near the stent wall is to increase the overall speed of the blood flow through the stent, thus leaving less time for blood platelets to attach to the vessel wall in the vicinity of the stent and cause clotting, thrombosis, or restenosis. The effect of the channels 50, 55 upon the overall speed of the blood flowing through the stent 10 is optimized to maximize efficacy without inducing any damage to the endothelium in the vicinity of the stent. Some of the variables that affect the speed of the flowing blood include the width, depth and shape of the channels, the pitch or spacing of the channels, and the total degree of curvature of the channels as they extend from the first end 24 to the second end 25 of the stent.

In a typical method of use of the stent of the present invention, the delivery of the stent 10 can be accomplished in a number of ways. The stent is first mounted onto an inflatable balloon on the distal extremity of a delivery catheter. The stent may be crimped down onto the balloon to ensure a low profile.

The catheter-stent assembly can be introduced within the patient's vasculature in a conventional Seldinger technique through a guide catheter as described. This technique entails disposing a guidewire through the lesion or damaged arterial section and subsequently advancing the catheter-stent assembly over the guidewire within the artery until the stent is directly adjacent the lesion. The balloon of the catheter is then expanded to expand the stent against the inside of the artery. The lesion may also be pre-dilated by an angioplasty balloon prior to the placement of the stent to pre-expand the treatment site. In some circumstances during the treatment of stenotic portions of an artery, the artery may have to be expanded considerably in order to facilitate passage of blood or other fluid therethrough.

Once the stent 10 has been deployed in the vessel, the balloon is deflated and the catheter withdrawn, thus allowing normal blood flow to resume through the vessel and the expanded stent. The inner layer 40 is expanded along with the tubular body 20 and prevents blood from contacting the vessel along the stent length by covering the stent inner surface 22 and all of the apertures 21 formed therein. The apertures are thereby no longer candidate sites for the formation of blood clots and thrombi, as is the case with prior art stents. It must be noted that the inner layer will also prevent the endothelialization of the stent as endothelial cells will not be able to extend through the apertures. The channel 50 will function to divert a small portion of the blood flowing through the stent and induce it to flow in a partially circumferential direction, thereby inducing a spin in the blood flow and causing it to flow therethrough at a higher rate of speed. Due to the faster flow of blood through the stent, blood platelets will be afforded a shorter period of time, and thus reduced opportunity, to attach themselves to the ends 24 or 25 of the stent, or to the vessel wall adjacent the stent, and it is therefore believed that the likelihood of blood clotting, thrombus formation, and restenosis will be reduced as well.

Figure 4:
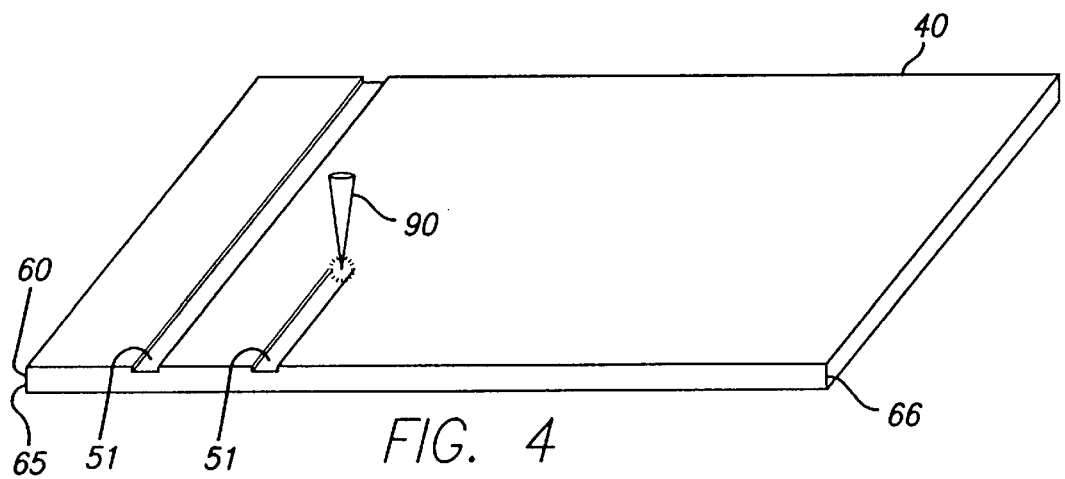
FIG. 4 is a perspective view depicting a layer having a flow channel formed thereon with a laser according to the invention.

With reference now to FIG. 4, in one method of forming the inner layer 40 according to the present invention, a flat polymeric material sheet 60 is exposed to a laser 90 that vaporizes the surface of the sheet to form parallel channels 51 on the surface thereof. Subsequently, opposite ends 65 and 66 of the polymeric sheet are joined together so that the sheet forms the tubular layer 40 and the channels 51 form a single, continuous, helical channel 50. Alternative means for forming the channels 51, such as cutting, pressing, or molding the polymeric sheet are also contemplated. Molding the inner layer may also be accomplished by casting the polymeric material onto a preformed mold to form the layer directly into the desired tubular shape with the channel 50.

Figure 5:
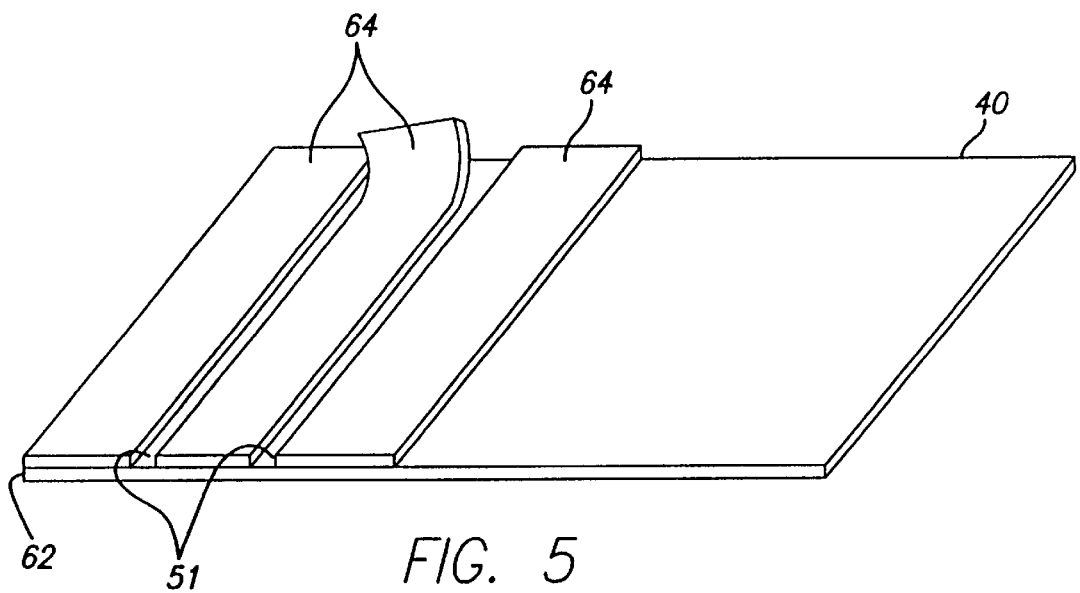
FIG. 5 is a perspective view of a layer depicting a flow channel formed thereon by strips disposed on its surface according to the invention.

Referring to FIG. 5, in one embodiment of forming the channel 50, flat polymeric material strips 64 are disposed on and attached to a polymeric material sheet 62 to define the channels 51 therebetween. The sheet 62 is subsequently formed into the desired tubular shape as described previously by rolling the sheet up and attaching the opposite sides thereof to one another.

Further modifications and improvements may additionally be made to the device disclosed herein without departing from the scope of the invention. Accordingly, it is not intended that the invention be limited, except as by the appended claims.

What is claimed:

1. A stent, comprising:

a radially expandable tubular body configured for initially being advanceable through a blood vessel and for supporting such blood vessel upon expansion therein, having an inner surface defining an inner lumen and having a first end and a second end; and a radially expandable layer having an outer surface attached to the entire inner surface of the tubular body and an inner surface having at least one channel therein extending between the first end and second end of the lumen.

2. The stent of claim 1, wherein the at least one channel is in the form of a helix.

3. The stent of claim 2, wherein said expandable layer is impermeable to blood.

4. The stent of claim 1, wherein the expandable layer inner surface has a plurality of channels thereon extending at an angle to the stent longitudinal axis.

5. The stent of claim 1, wherein the layer is formed of a polymeric material.

6. The stent of claim 5, wherein the polymeric material is silastic rubber.

7. The stent of claim 5, wherein the polymeric material is Teflon©.

8. The stent of claim 1, wherein said expandable layer is impermeable to blood.

* * * * *